(12) United States Patent
Veldur et al.

(10) Patent No.: US 11,786,684 B2
(45) Date of Patent: Oct. 17, 2023

(54) CRICOTHYROTOMY DEVICE

(71) Applicants: Rishab Rao Veldur, Marietta, GA (US); Eric Simon, Marietta, GA (US); Katherine McNeice, Marietta, GA (US)

(72) Inventors: Rishab Rao Veldur, Marietta, GA (US); Eric Simon, Marietta, GA (US); Katherine McNeice, Marietta, GA (US)

( * ) Notice: Subject to any disclaimer, the term of this patent is extended or adjusted under 35 U.S.C. 154(b) by 830 days.

(21) Appl. No.: 16/723,616

(22) Filed: Dec. 20, 2019

(65) Prior Publication Data

US 2021/0187227 A1 Jun. 24, 2021

(51) Int. Cl.
*A61M 16/04* (2006.01)
*A61M 16/00* (2006.01)
*A61B 17/3211* (2006.01)
*A61M 25/00* (2006.01)

(52) U.S. Cl.
CPC ...... *A61M 16/0472* (2013.01); *A61B 17/3211* (2013.01); *A61M 16/0084* (2014.02); *A61M 25/0009* (2013.01)

(58) Field of Classification Search
CPC . A61B 17/34; A61B 17/3415; A61B 17/3421; A61B 17/3211; A61B 2017/32113; A61B 17/3209; A61M 16/0472; A61M 16/0465; A61M 16/0497; A61M 16/0429
See application file for complete search history.

(56) References Cited

U.S. PATENT DOCUMENTS

| | | | | | |
|---|---|---|---|---|---|
| 3,384,087 | A | * | 5/1968 | Brummelkamp | A61M 16/0472 128/207.29 |
| 4,556,059 | A | * | 12/1985 | Adamson, Jr. | A61M 16/0472 128/207.14 |
| RE34,086 | E | * | 10/1992 | George | A61M 16/0472 128/200.26 |
| 8,151,791 | B2 | * | 4/2012 | Arlow | A61M 16/0472 128/207.14 |
| 8,215,309 | B2 | * | 7/2012 | Single, Jr. | A61B 17/32093 128/207.14 |
| 2005/0148936 | A1 | * | 7/2005 | Moss | A61B 17/3403 604/116 |
| 2010/0275911 | A1 | * | 11/2010 | Arlow | A61M 16/0472 128/207.29 |
| 2011/0041854 | A1 | * | 2/2011 | Rasor | A61M 16/0472 128/207.15 |
| 2012/0253316 | A1 | * | 10/2012 | Oktavec | A61B 17/1757 604/103.05 |

(Continued)

OTHER PUBLICATIONS

Collopy, K.T., "CE Article: Surgical Cricothyrotomies in Prehospital Care", EMS World, https://www.emsworld.com/206071/ce-article-surgical-cricothyrotomies-prehospital-care, Jan. 2015 available online Dec. 5, 2014 (13 pages).

(Continued)

*Primary Examiner* — Sarah W Aleman
(74) *Attorney, Agent, or Firm* — Wilmer Cutler Pickering Hale and Dorr LLP

(57) ABSTRACT

A cricothyrotomy device comprises an incision member and an insertion member that are joined together but separable. The incision member further comprises a scalpel, a scalpel cap, a spring assembly, and an incision holder. The insertion member comprises a cannula, a cannula cap, and an insertion handle.

16 Claims, 7 Drawing Sheets

(56) References Cited

U.S. PATENT DOCUMENTS

2019/0314059 A1* 10/2019 Coppedge ............ A61B 17/164

OTHER PUBLICATIONS

Google Shopping Search, "Cricothyrotomy kit", https://www.google.com/search?q=cricothyrotomy+kit&source=univ&tbm=shop&tbo=u&sa=X&ved=0ahUKEwjoiPzUhlfhAhVrm-AKHVqvBJwQsxglLQ& . . . , accessed Nov. 20, 2020 (5 pages).
Hessert, M. Josephine et al., "Optimizing Emergent Surgical Cricothyrotomy for use in Austere Environments", Wilderness & Environmental Medicine, 24:53-66, 2013 (14 pages).
Video: "Actual cricothyroidotomy with disclaimer", https://www.youtube.com/watch?v=R-ViSEzNM5k&feature=youtu.be, uploaded Sep. 25, 2016 (1 page).
Video: "Bougie-Aided Cricothyrotomy by Darren Braude", http://www.youtube.com/watch?v=wVQFJR7pmrQ&feature=youtu.be, uploaded Apr. 13, 2010 (3 pages).
Video: "Cricothyrotomy in Afghanistan", https://www.youtube.com/watch?v=SBuoULSKMgQ&feature=youtu.be, uploaded Apr. 21, 2014 (4 pages).
Video: "Cricothyrotomy, Iraq 2017", https://www.youtube.com/watch?v=tFRdSP1F_gg&feature=youtu.be, uploaded Nov. 3, 2018 (1 page).
Video: "EMCrit Podcast 231—How to Practice Cricothyroidotomy (Cric)", https://www.youtube.com/watch?v=uaJpTqanr3A&feature=youtu.be, uploaded Aug. 25, 2018 (3 pages).
Video: "Emergency Cricothyroidotomy using CricKey", https://www.youtube.com/watch?v=C018REpwtIE&feature=youtu.be, uploaded Jul. 9, 2018 (3 pages).
Video: "Surgical Airway (Cricothyrotomy) Performed by Ram Parekh", https://www.youtube.com/watch?v=1iPRrzO26el, uploaded Jul. 15, 2020 (3 pages).

* cited by examiner

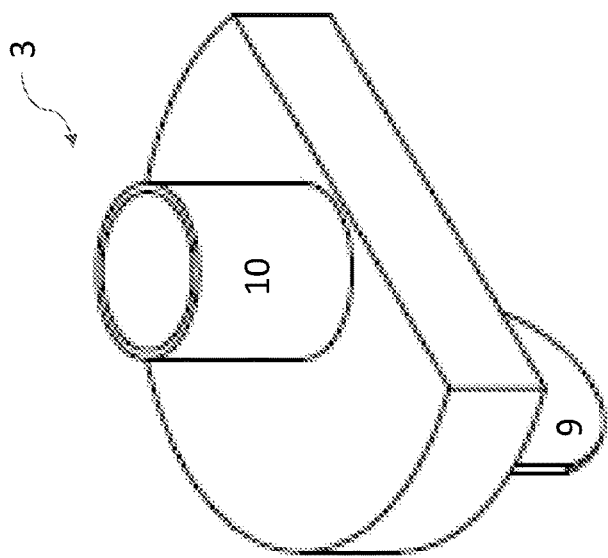
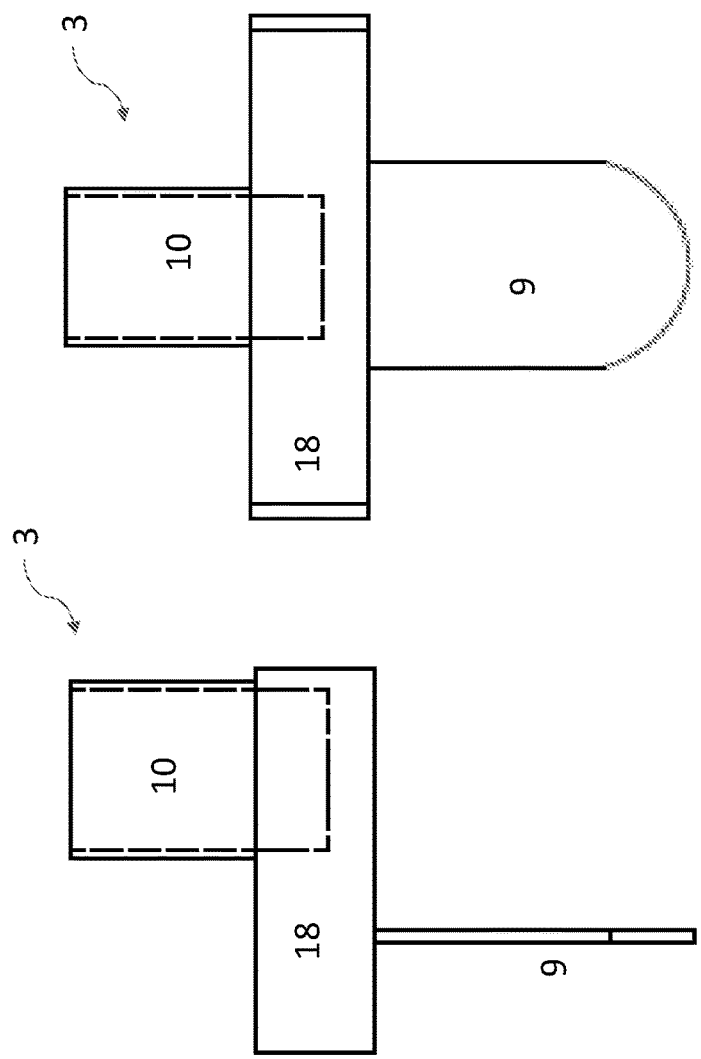
FIG. 2F
FIG. 2E
FIG. 2D

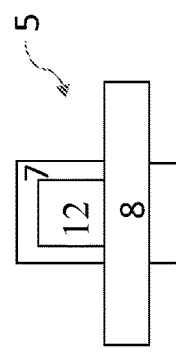
FIG. 3D
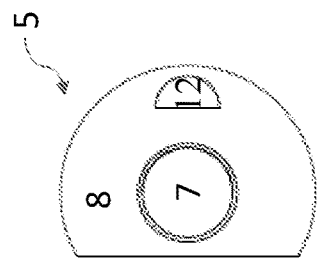
FIG. 3F
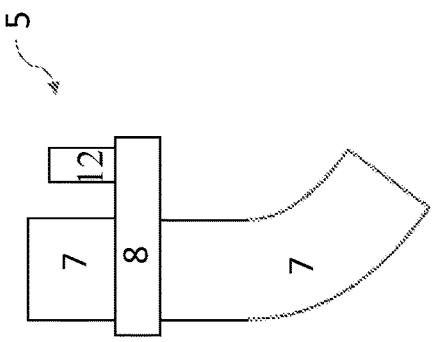
FIG. 3C
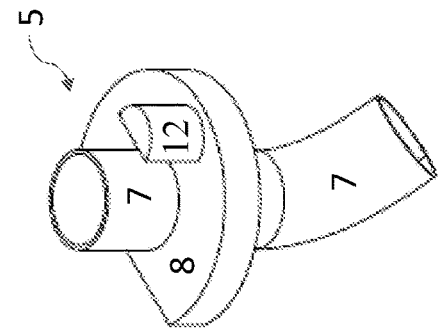
FIG. 3E
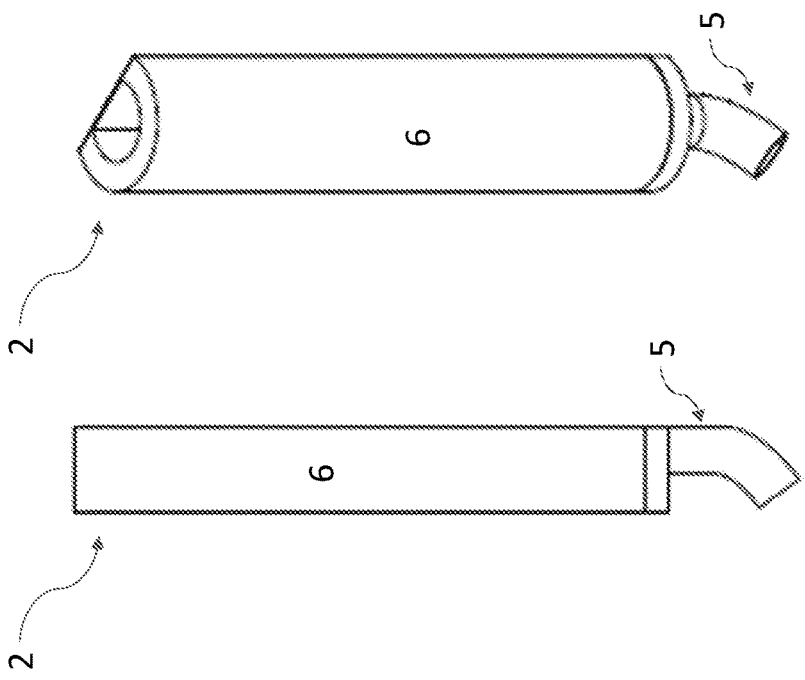
FIG. 3B
FIG. 3A

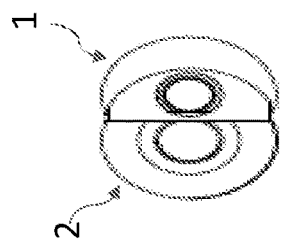
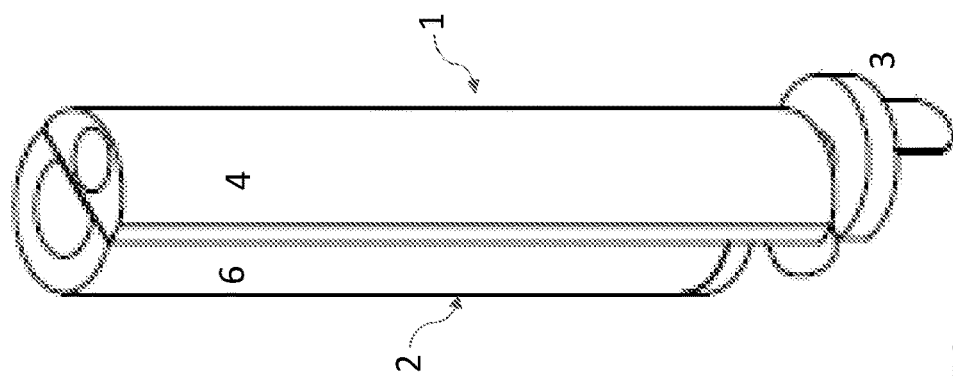
FIG. 5D
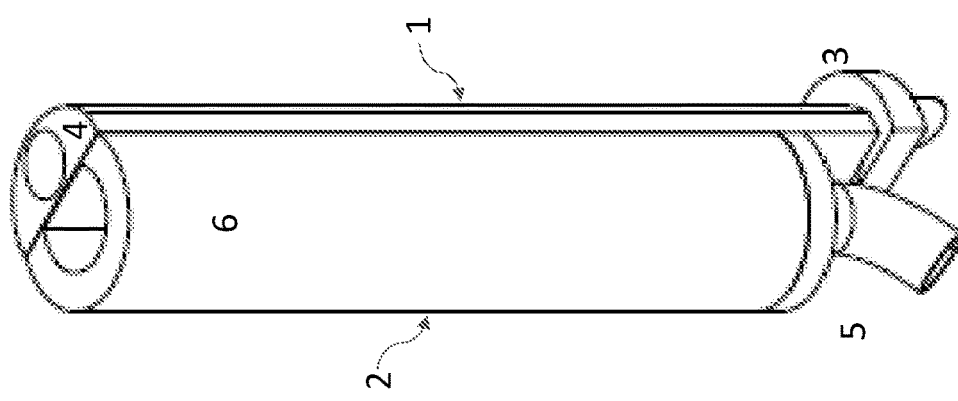
FIG. 5C
FIG. 5B
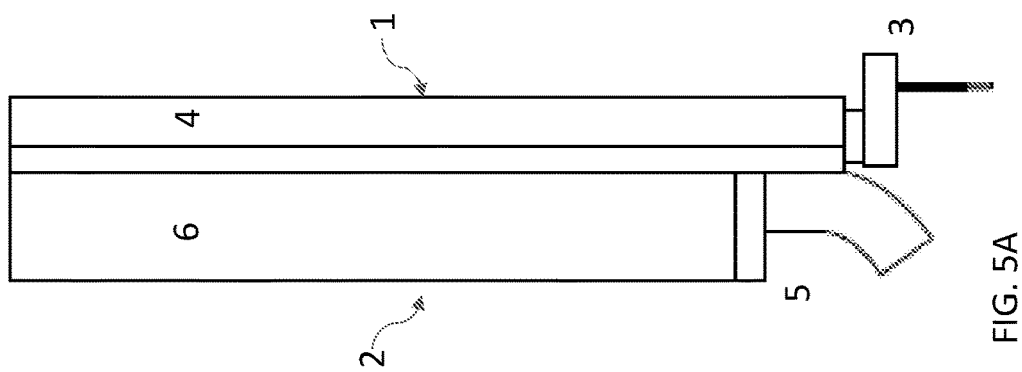
FIG. 5A

CRICOTHYROTOMY DEVICE

FIELD OF DISCLOSURE

The present disclosure generally relates to a device for performing cricothyrotomy.

BACKGROUND

Cricothyrotomy is an emergency procedure performed on patients who are not able to breath due to severe facial trauma or other airway obstructions. A physician or a paramedic creates an incision into the cricothyroid membrane to build an artificial airway that can help the patient breath through external means such as a ventilator or a self-inflating bag. Traditionally, multiple tools are required for cricothyrotomy, including, among others, a scalpel, a bougie, and tracheal spreaders. At the same time, multiple steps are involved in the procedure, often including multiple incisions and placement of different devices. Importantly, the incisions have to be performed with great care to avoid excessive depth that can cause injury to the underlying esophagus.

A major issue of cricothyrotomy originates from the type of environment in which they are performed. Combat situations, in particular, pose significant challenges due to the severity of injuries, shortage of paramedic personnel and time, and lack of clean, secure, or stable locations to perform the cricothyrotomy procedure. As an example, cricothyrotomies sometimes need to be performed by a single combat medic in flying helicopters. Traditional cricothyrotomy requiring multiple tools and involving multiple steps thus renders the procedure especially challenging and prone to failure and fatality.

SUMMARY

Inventors have recognized that there is a need for a cricothyrotomy system that can enable the medical personnel to perform cricothyrotomies fast and efficiently, particularly in challenging situations, such as combat environments.

The present invention relates to a device for performing cricothyrotomy.

In one aspect, a cricothyrotomy device includes an incision member and an insertion member. The incision member further includes an incision holder, a scalpel assembly and a spring assembly. The scalpel assembly includes a scalpel and a scalpel cap that is attached to the distal end of the scalpel and broader than the scalpel. The spring assembly includes a compression spring. The insertion member includes an insertion handle and a cannula assembly, with the cannula assembly further including a cannula suitable for insertion into human trachea, and a cannula cap that is attached to the distal end of the cannula and broader than the cannula.

In some embodiments, the incision member and the insertion member include one or more connectors capable of connecting the incision member and the insertion members together.

In some embodiments, the cannula assembly includes one or more connectors capable of connecting the cannula assembly to the insertion handle.

In some embodiments, the cannula is curved.

In some embodiments, the inner cavity of the cannula has an internal diameter of 8 mm.

In some other embodiments, the inner cavity of the cannula has an internal diameter that is less than 8 mm, such as 7 mm, 6 mm, 5 mm, 4 mm, 3 mm and the like. Such smaller sizes may be beneficial when performing cricothyrotomy on patients that are younger, such as less than 8 years old.

In some embodiments, some or all components are made of polylactic acid.

In some embodiments, some or all of the components are 3D-printed.

In one aspect, a method to perform cricothyrotomy is disclosed which includes an operator placing the cricothyrotomy device above the cricothyroid area of a person in need of cricothyrotomy and pushing down the device. The scalpel in the incision member may be designed so that the depth of the incision made to the patient does not exceed a predetermined depth, such as by limiting further penetration by use of a compression spring designed to provide a specified depth of incision and/or by use of a scalpel cap designed to limit further depth of incision when the scalpel cap touches the skin. The operator then separates the insertion member from the incision member. While removing the incision member from the neck incision, the operator slides the insertion member into the incision until it is stopped by the broad cannula cap that stays over the skin. The insertion handle is then separated from the cannula and the distal end of the cannula is connected to an external airway or oxygen source.

In some embodiments, the distal end of the cannula is connected to an external oxygen source.

In some embodiments, the external oxygen source is a ventilator.

In some other embodiments, the external oxygen source is a self-inflating bag.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

FIGS. 2D-2G illustrate the scalpel assembly (3) of the incision member (1) from different views.

FIGS. 3A-B illustrate additional details of an insertion member (2) in accordance with certain embodiments.

FIGS. 3C-F illustrates the cannula assembly (5) of the insertion member (2) from different views.

FIGS. 5A-5D illustrate different views of the entire cricothyrotomy device of the current invention, with the incision member (1) and the insertion member (2) attached to each other.

DETAILED DESCRIPTION

The present disclosure relates to a device for performing a cricothyrotomy. To the extent that the following description is of a specific embodiment or a particular method of use, it is intended to be illustrative only, and not limiting of the claimed invention. The following description is intended to cover all alternatives, modifications, and equivalents that are included in the spirit and scope of the invention, as defined in the claims.

The cricothyrotomy device in accordance with certain embodiments can be easily and efficiently used for performing cricothyrotomy in challenging environments, such as in combat situations.

Figure 1A:
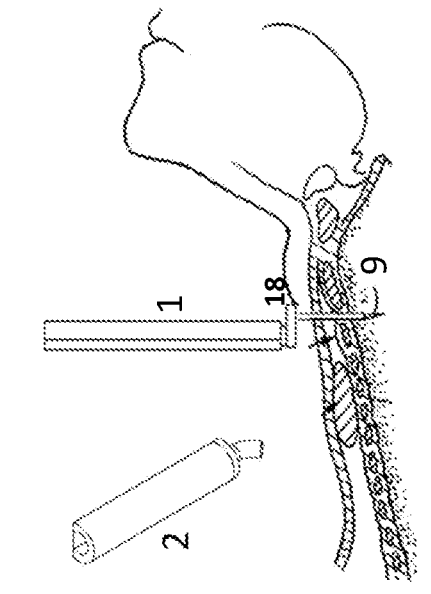
FIGS. 1A-1D illustrate a procedure of performing cricothyrotomy in accordance with certain embodiments.
Figure 1B:
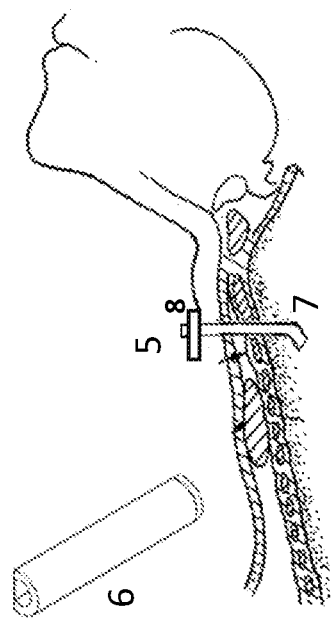
Figure 1C:
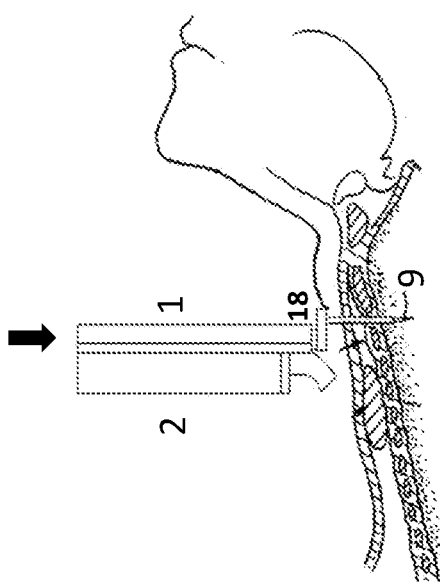
Figure 1D:
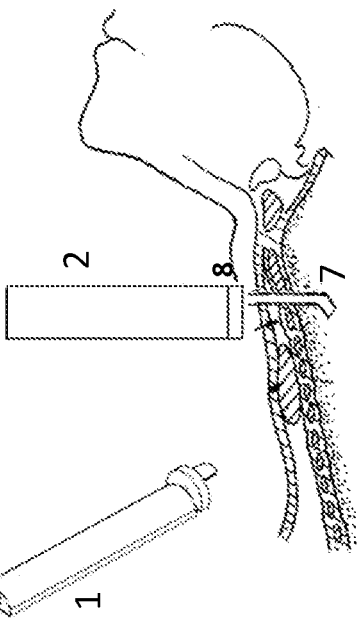

FIGS. 1A-1D illustrate a procedure of performing cricothyrotomy in accordance with certain embodiments. As shown in FIGS. 1A-1D, the cricothyrotomy device in accordance with certain embodiments contains an incision member (1) and an insertion member (2). The incision member (1) includes a scalpel cap (18) that is provided with a scalpel (9). As shown in FIG. 1, the cricothyrotomy operator first places the cricothyrotomy device onto the neck area of a patient above a cricothyroid membrane, with the scalpel (9) facing the location of the incision to be made. The operator then pushes down the device. As depicted in FIG. 1A, the scalpel (9) creates a horizontal incision through both the skin and the cricothyroid membrane. The scalpel cap (18) stays above the skin and ensures that the scalpel does not penetrate too far and that the incision does not exceed a predetermined depth. In FIG. 1B, the operator separates the insertion member (2) from the incision member (1). Then, as shown in FIG. 1C, while retrieving the incision member (1) from the incision in the neck, the operator also slides the separated insertion member (2) into the incision until it is stopped by the cannula cap (8) that stays over the skin. Then, as shown in FIG. 1D, the insertion handle (6) is removed from the cannula assembly (5) and the cannula (7) is ready to be connected to an external airway or oxygen source. Accordingly, the incision member (1) can create an incision of the cricothyroid membrane and the insertion member (2) can then be separated from the incision member and inserted into the trachea through the incision. The cannula (7) in the insertion member (2) stays in trachea and provides an artificial airway.

Figure 2C:
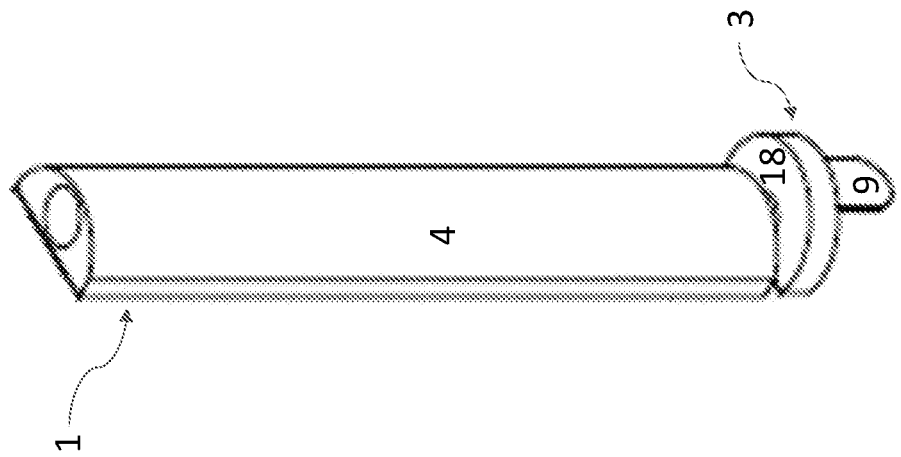
FIGS. 2A-2C illustrate additional details of an incision member (1) in accordance with certain embodiments.
Figure 2B:
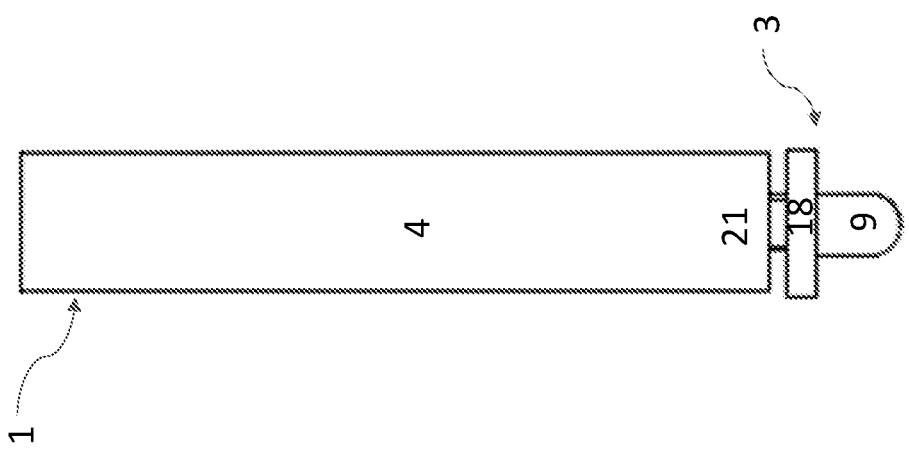
Figure 2A:
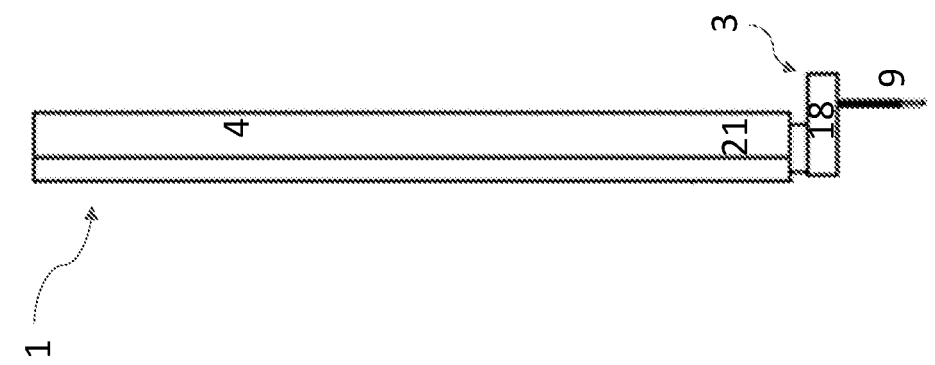
Figure 2H:
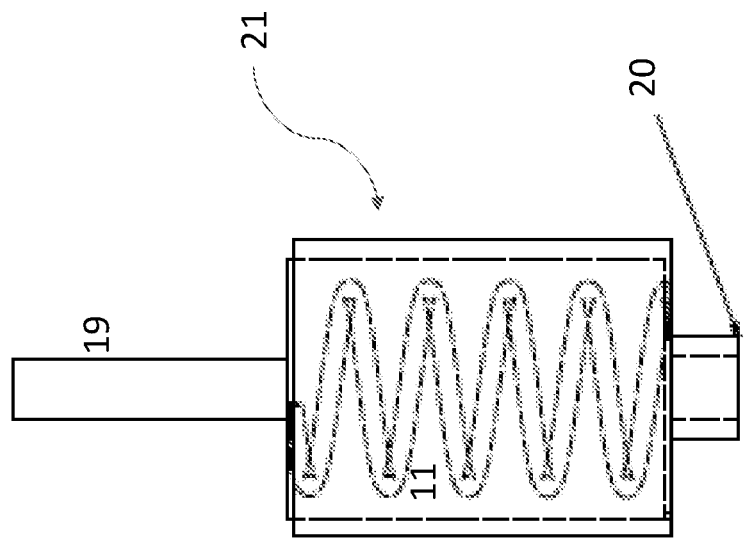
FIG. 2H is an amplified view of the compression spring (11) through the incision holder (4).
Figure 2G:
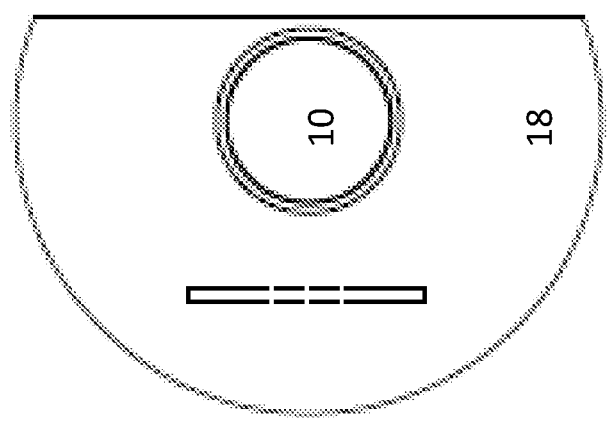

FIGS. 2A-2I show additional details of the incision member (1) in accordance with certain embodiments. FIGS. 2A and 2B show different side view of the incision member (1) and FIG. 2C shows a tilted side view of the incision member (1) showing its top surface. As shown, the incision member (1) includes an incision holder (4), a scalpel assembly (3), and a spring assembly (21 in FIG. 2H, hidden from view in FIGS. 2A-2C). As shown in FIGS. 2D-2G, the scalpel assembly (3) includes a scalpel (9), a scalpel cap (18) and a connector (10). The scalpel (9) is attached to the broader scalpel cap (18). Inside connector (10) can be placed a proximal rod (20) that touches the distal surface of the scalpel cap (18). Over the proximal rod (20) can be placed a compression spring (11) over which a distal rod (19) can be placed. The combination of proximal rod (2), compression spring (11) and distal rod (19) can be placed inside the incision holder (4) such that it is not visible from outside views. However, when the operator pushes down the incision member (1) onto the neck area above the cricothyroid membrane, the pressure is directed to the compression spring (11) through the distal rod (19). Through the proximal rod (20), the spring (11) then pushes the scalpel (9) to self deploy and create a horizontal incision through the skin and the cricothyroid membrane. The compression spring can be configured to reach a desired depth of the incision. As discussed above, the broader scalpel cap (18) can be designed to stay above the skin and ensure that the incision does not exceed a predetermined depth.

FIGS. 3A-3B show additional details of the insertion member (2). As shown, the insertion member (2) includes an insertion handle (6) and a cannula assembly (5). The insertion member (2) can be inserted into the tracheal passing through an incision created by the incision member (1). The insertion handle (6) can then be separated from the cannula assembly (5), which can stay in the trachea and provides an artificial airway.

FIGS. 3C-3F show additional details of the cannula assembly (5) from different views. The cannula assembly comprises a cannula (7) and a cannula cap (8). The cannula (7) can become a part of the artificial airway for the patient after the cricothyrotomy is finished. The cannula (7) as depicted in FIGS. 3C-3F is curved in accordance with some embodiments. However, other shapes are possible as will be readily apparent to one skilled in the art.

The broader cannula cap (8) can be designed to be fixed to the cannula (7) and to stay above the skin, preventing the cannula (7) from inserting too deep into the trachea and causing unnecessary tissue damage. The cannula cap (8) can include further mechanisms such as a connector (12) to facilitate joining with the insertion handle (6).

Figure 4B:
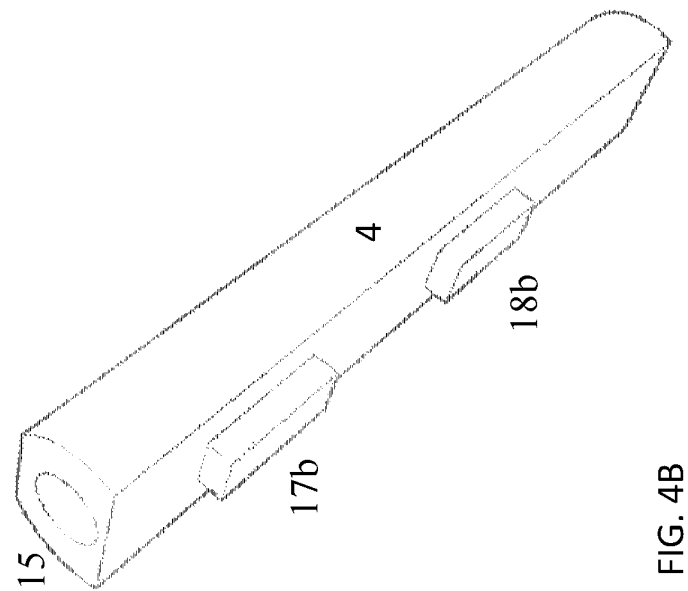
FIGS. 4A and 4B illustrate the connectors (17a, 17b, 18a, and 18b) for joining the incision holder (4) of the incision member (1) to the insertion handle (6) of the insertion member (2), and connectors (13, 14) on the insertion handle (6) for joining the cannula assembly (5 in FIG. 3, not shown in FIG. 4) to the insertion handle (6), as well as the connector (15) on the incision holder (4) for joining the scalpel assembly (3 in FIG. 3, not shown in FIG. 2) to the incision holder (4).
Figure 4A:
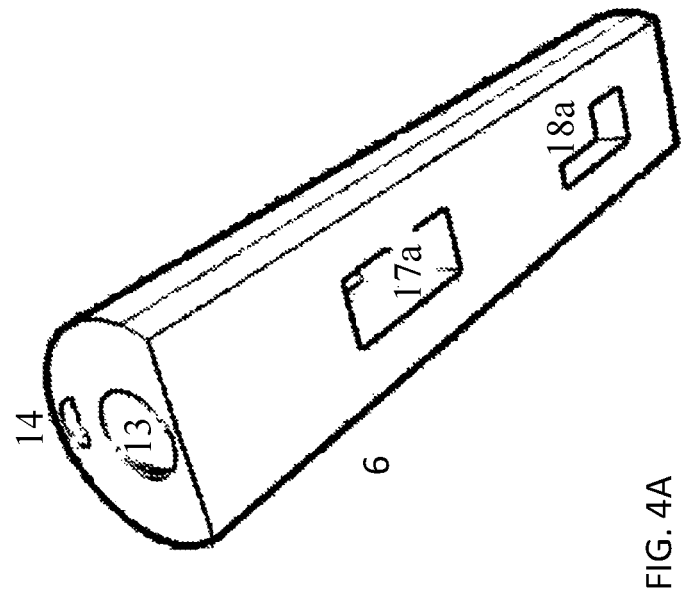

FIGS. 4A-4B illustrate how the incision member (1) and insertion member (2) can be connected to each other. The incision member (1) and the insertion member (2) can be joined via one or more pairs of connectors. One embodiment of the connectors is shown in FIGS. 4A and 4B, where the insertion handle (6) of the insertion member (2) has two female connectors (17a and 18a) on the flat surface, and the incision holder (4) of the incision member (1) has two corresponding male connectors (17b and 18b). In other embodiments, the female connectors can be placed in the incision holder (4) and the corresponding male connectors can be placed on the insertion handle (6). Other types of connectors can be utilized, including but not limited to hook-and-loop fasteners, magnetic connectors, snap connectors, clips, thumb screws, breakable adhesive glue straps.

Moreover, as shown in FIG. 4A, the proximal end of the insertion handle (6) can be provided with connectors to connect to the cannula assembly (5). One embodiment of the connectors is shown in FIG. 4A, in which two female connectors are provided—a first female connector (13) for the cannula (7), and a second female connector (14) for connector (12) on the cannula cap (8). The two pairs of connectors can allow the cannula assembly (5) to be attached to the insertion handle (6). After the insertion member (2) is already inserted in the trachea, the operator can press down the cannula cap (8) and keep the cannula cap (8) and the cannula (7) at the inserted position, and pull the insertion handle (6) away from the cannula assembly (5) by separating the connector pairs.

The proximal end of the incision holder (4) can be provided with one or more connector to connect to the scalpel assembly (3). One embodiment of the connectors is shown in FIG. 4B, in which one female connector (15) is provided for the connector (10) on the scalpel cap (18) that is shown in FIGS. 2D-2G.

FIGS. 5A-5D illustrate the fully assembled cricothyrotomy device of the present disclosure. FIG. 5A and FIG. 5B are side views, FIG. 5C is a tilted side view showing the top surface of the assembly, and FIG. 5D is a direct view of the top surface of the assembly. The incision member (1) and the insertion member (2) are joined by the connectors shown in FIGS. 4A-4B. Each member can be easily separated from the other by disconnection the connectors with slight force.

The cricothyrotomy device described herein, which includes the incision member (1) and insertion member (2), provides a complete medical mechanism for performing cricothyrotomy. No other device or tool is required. The two members can be attached to each other via connectors to make the invention a one-piece device. The insertion member (2) can be easily separated from incision member (1) after the incision. It is a great advantage for cricothyrotomy in challenging environments such as combat situation to have an "all-in-one" device instead of multiple tools, as required in traditional cricothyrotomy methods. It makes the procedure faster, easier to manage and less prone to errors and failure.

Moreover, the depth of incision by the scalpel (9) and the depth of insertion by the cannula (7) can be well controlled, because of their respective scalpel cap (18) and cannula cap (8) that will allow the remaining components to stay above the skin and therefore limit the penetration of the scalpel and the cannula. This built-in control mechanism practically eliminates the frequent cricothyrotomy issues due to excessive depth of incisions. It is again a great advantage since the traditional methods require great care in controlling the incision depth, rendering the procedure time-consuming, challenging, and prone to tissue injury and failure.

When the person in need of cricothyrotomy is an adult or older than 8, the inner cavity of the cannula may have an internal diameter of 8 mm. When the person in need of cricothyrotomy is 8 years or younger, the inner cavity of the cannula may have an internal diameter that is less than 8 mm. In certain embodiments, one way of calculating the proper size of the inner cavity of the cannula for children may be using the equation: inner diameter=((age in years/4)+4) mm.

In addition, discarded cricothyrotomy tools, as discarded medical devices and tools in general, pose a serious threat to the environment. In one embodiment of the invention, some or all components of this invention are made of degradable polylactic acid. In another embodiment, some or all components of this invention are manufactured by 3-D printing.

In some embodiments, the distal end of the cannula is connected to an external oxygen source.

In some embodiments, the external oxygen source is a ventilator.

In some other embodiments, the external oxygen source is a self-inflating bag.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

The invention claimed is:

1. A cricothyrotomy device comprising:
    an incision member and an insertion member;
    wherein the incision member comprises an incision holder, a scalpel assembly and a spring assembly;
    wherein the incision holder has a first longitudinal flat surface, the first longitudinal flat surface having one or more protrusions,
    wherein the scalpel assembly comprises a scalpel and a scalpel cap attached to a distal end of the scalpel,
    wherein the distal end of the scalpel is the end further away from the cricothyroid area of a person in need of cricothyrotomy,
    wherein the scalpel cap is broader than the scalpel,
    wherein the spring assembly comprises a compression spring,
    wherein the insertion member comprises an insertion handle and a cannula assembly;
    wherein the insertion handle has a second longitudinal flat surface, the second longitudinal flat surface having one or more recessions,
    wherein the cannula assembly comprises a cannula suitable for insertion into human trachea, and a cannula cap attached to the distal end of the cannula, the cannula cap being broader than the cannula,
    wherein the incision member and the insertion member can be separated and reconnected,
    wherein the first longitudinal flat surface of the incision holder and second longitudinal flat surface of the insertion handle are adjoined when the incision member and the insertion member are connected.

2. The cricothyrotomy device of claim 1, wherein the incision holder and the insertion handle each comprise one or more connectors capable of connecting the incision member and the insertion members together.

3. The cricothyrotomy device of claim 2, wherein the one or more connectors comprise one or more female connectors and corresponding male connectors, wherein the one or more female connectors are on the insertion handle when the corresponding one or more male connectors are on the incision holder.

4. The cricothyrotomy device of claim 3, wherein the female connector is a recession on the first longitudinal flat surface of the insertion handle, and the corresponding male connector is a protrusion on the second longitudinal flat surface of the incision holder.

5. The cricothyrotomy device of claim 4, wherein the first longitudinal flat surface of the insertion member and the second longitudinal flat surface of the incision member are adjoined to each other when the corresponding male and female connectors on the incision holder and insertion handle are connected.

6. The cricothyrotomy device of claim 5, wherein the cannula assembly and the insertion handle can be separated and reconnected, and wherein the cannula assembly and the insertion handle comprise one or more connectors capable of connecting the cannula assembly to the insertion handle.

7. The cricothyrotomy device of claim 6, wherein the scalpel assembly and the incision holder can be separated and reconnected through an inside connector.

8. The cricothyrotomy device of claim 7, wherein the cannula is curved.

9. The cricothyrotomy device of claim 8, wherein the cannula has an internal diameter of 8 mm.

10. The cricothyrotomy device of claim 8, wherein the inner cavity of the cannula has an internal diameter that is calculated based on the age of the patient to be treated according to the equation when the age of the patient is 8 years or younger:

inner diameter=((age in years/4)+4) mm.

11. The cricothyrotomy device of claim 10, wherein one or more components are made of polylactic acid.

12. The cricothyrotomy device of claim 11, wherein one or more of the components are 3D-printed.

13. A method to perform a cricothyrotomy, comprising
placing a cricothyrotomy device above the cricothyroid area of a person in need of cricothyrotomy, the cricothyrotomy device comprising an incision member and an insertion member;
wherein the incision member comprises an incision holder, a scalpel assembly and a spring assembly;
wherein the incision holder has a first longitudinal flat surface, the first longitudinal flat surface having one or more protrusions,
wherein the scalpel assembly comprises a scalpel and a scalpel cap attached to a distal end of the scalpel,
wherein the distal end of the scalpel is the end further away from the cricothyroid area of a person in need of cricothyrotomy,
wherein the scalpel cap is broader than the scalpel,
wherein the spring assembly comprises a compression spring,
wherein the insertion member comprises an insertion handle and a cannula assembly;
wherein the insertion handle has a second longitudinal flat surface, the second longitudinal flat surface having one or more recessions,
wherein the cannula assembly comprises a cannula suitable for insertion into human trachea, and a cannula cap attached to the distal end of the cannula, the cannula cap being broader than the cannula,
wherein the incision member and the insertion member can be separated and reconnected,
wherein the first longitudinal flat surface of the incision holder and second longitudinal flat surface of the insertion handle are adjoined when the incision member and the insertion member are connected,
pushing down the device and thereby creating an incision, wherein the scalpel in the incision member cannot cut deeper than when the scalpel cap touches the skin,
separating the insertion member from the incision member while the scalpel is in the skin incision, wherein the separating comprises separating of the one or more protrusions on the first longitudinal flat surface of the incision holder and the one more recessions on the second longitudinal flat surface of the insertion handle,
removing the incision member from the incision,
sliding the insertion member into the incision until it is stopped by the cannula cap that stays over the skin;
separating the insertion handle from the cannula.

14. The method of claim 13, wherein the distal end of the cannula is connected to an external oxygen source.

15. The method of claim 14, wherein the external oxygen source is a ventilator.

16. The method of claim 15, wherein the external oxygen source is a self-inflating bag.

\* \* \* \* \*